US011829184B1

(12) United States Patent
Wright

(10) Patent No.: US 11,829,184 B1
(45) Date of Patent: Nov. 28, 2023

(54) HEALTH EVENT HIGHLIGHTER

(71) Applicant: Verily Life Sciences LLC, Mountain View, CA (US)

(72) Inventor: David Wright, Burlingame, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 215 days.

(21) Appl. No.: 16/141,753

(22) Filed: Sep. 25, 2018

Related U.S. Application Data

(60) Provisional application No. 62/565,653, filed on Sep. 29, 2017.

(51) Int. Cl.
*G06F 3/04817* (2022.01)
*G16H 40/63* (2018.01)
(Continued)

(52) U.S. Cl.
CPC .......... *G06F 3/04817* (2013.01); *G06F 9/451* (2018.02); *G16H 10/60* (2018.01);
(Continued)

(58) Field of Classification Search
CPC .. G06F 3/04817; G06F 9/451; G06F 11/3476; G06F 2201/86; G06F 2201/865;
(Continued)

(56) References Cited

U.S. PATENT DOCUMENTS

| 8,398,546 | B2 * | 3/2013 | Pacione | A61B 5/411 |
| | | | | 128/920 |
| 8,771,183 | B2 * | 7/2014 | Sloan | H04B 7/24 |
| | | | | 600/300 |

(Continued)

FOREIGN PATENT DOCUMENTS

| EP | 2301428 B1 * | 11/2016 | ............. A61B 5/145 |
| WO | WO-2017131328 A1 * | 8/2017 | ............. G06F 19/00 |

OTHER PUBLICATIONS https://www.youtube.com/watch?v=X7pa9jCJNoY; published Apr. 12, 2016; 1 page.

(Continued)

*Primary Examiner* — Jonathan Ng
*Assistant Examiner* — Hunter J Rasnic
(74) *Attorney, Agent, or Firm* — Perkins Coie LLP

(57) ABSTRACT

Introduced here is a method, a system, a device, etc. for displaying health-related data (e.g., blood glucose measurements) relevant to user's selection. The method, the system, the device, etc. can be based on: receiving healthcare-related data from data streams associated with a profile of a patient; identifying, based on a least a subset of the data streams, a time window corresponding to a contextual event indicative of a patient activity that has a potential of affecting metabolism of the patient; determining a graphical representation of the contextual event; generating a graph of blood glucose level over time for display; detecting a user indication of a user interest in a time point along the graph of the blood glucose level; and highlighting the graphical representation of the contextual event in response to the time point falling within the identified time window.

20 Claims, 7 Drawing Sheets

(51) Int. Cl.
*G06F 9/451* (2018.01)
*G16H 10/60* (2018.01)
*G16H 20/60* (2018.01)
*G16H 50/50* (2018.01)

(52) U.S. Cl.
CPC ............ *G16H 20/60* (2018.01); *G16H 40/63* (2018.01); *G16H 50/50* (2018.01)

(58) Field of Classification Search
CPC ........ G16H 20/60; G16H 40/63; G16H 40/67; G16H 50/30; G16H 50/70; G01N 33/48; A61B 5/02438; A61B 5/14532; H04W 4/38; A61M 5/14; A61M 5/1723; A61M 2230/201
See application file for complete search history.

(56) References Cited

U.S. PATENT DOCUMENTS

| | | | | |
|---|---|---|---|---|
| 8,798,934 | B2* | 8/2014 | Wei | A61B 5/746 |
| | | | | 702/19 |
| 8,974,385 | B2* | 3/2015 | Lee | G16H 50/70 |
| | | | | 600/300 |
| 9,398,854 | B2* | 7/2016 | Proud | H02J 50/20 |
| 9,465,917 | B2* | 10/2016 | Soni | G06F 19/00 |
| 9,532,716 | B2* | 1/2017 | Proud | H02J 50/10 |
| 9,662,053 | B2* | 5/2017 | Richards | A61B 5/02427 |
| 9,737,214 | B2* | 8/2017 | Proud | H02J 50/10 |
| 2005/0113650 | A1* | 5/2005 | Pacione | A61B 5/4809 |
| | | | | 600/300 |
| 2009/0240127 | A1* | 9/2009 | Ray | G16H 40/63 |
| | | | | 600/300 |
| 2010/0075353 | A1* | 3/2010 | Heaton | A61B 5/0002 |
| | | | | 435/14 |
| 2010/0105999 | A1* | 4/2010 | Dixon | A61B 5/150022 |
| | | | | 600/347 |
| 2011/0053121 | A1* | 3/2011 | Heaton | A61B 5/1495 |
| | | | | 600/365 |
| 2011/0264378 | A1* | 10/2011 | Breton | A61B 5/0002 |
| | | | | 702/19 |
| 2012/0095691 | A1* | 4/2012 | Galley | G16H 40/63 |
| | | | | 702/19 |
| 2012/0149996 | A1* | 6/2012 | Stivoric | G16H 40/63 |
| | | | | 600/301 |
| 2012/0266251 | A1* | 10/2012 | Birtwhistle | H04W 12/50 |
| | | | | 726/26 |
| 2013/0035871 | A1* | 2/2013 | Mayou | G16H 50/20 |
| | | | | 702/26 |
| 2014/0068487 | A1* | 3/2014 | Steiger | A61B 5/14532 |
| | | | | 715/771 |
| 2014/0074850 | A1* | 3/2014 | Noel | G06F 11/0709 |
| | | | | 707/741 |
| 2014/0188398 | A1* | 7/2014 | Cohen | A61B 5/746 |
| | | | | 702/19 |
| 2014/0206970 | A1* | 7/2014 | Wesley | A61B 5/14532 |
| | | | | 600/365 |
| 2014/0276167 | A1* | 9/2014 | Dasgupta | A61B 5/4818 |
| | | | | 600/529 |
| 2015/0289823 | A1* | 10/2015 | Rack-Gomer | A61B 5/14532 |
| | | | | 600/365 |
| 2015/0347698 | A1* | 12/2015 | Soni | G06K 9/6218 |
| | | | | 706/11 |
| 2016/0098848 | A1* | 4/2016 | Zamanakos | G16H 15/00 |
| | | | | 345/440 |
| 2016/0174853 | A1* | 6/2016 | Cho | A61B 5/4261 |
| | | | | 600/301 |
| 2017/0070414 | A1* | 3/2017 | Bell | H04L 41/064 |
| 2017/0251982 | A1* | 9/2017 | Koehler | A61B 5/7275 |
| 2018/0042558 | A1* | 2/2018 | Cabrera, Jr. | G16H 50/30 |
| 2018/0199890 | A1* | 7/2018 | Hayter | G16H 50/30 |

OTHER PUBLICATIONS

"Diabetes Tracker", https://www.youtube.com/watch?v=UFTZ9ACdoM0; YouTube image retrieved Nov. 2, 2018;, Aug. 7, 2016, 1 page.

"Glooko Diabetes Remote Monitoring Population Management", https://www.glooko.com; image retrieved from Internet on Nov. 2, 2018.

* cited by examiner

HEALTH EVENT HIGHLIGHTER

CROSS-REFERENCE TO RELATED APPLICATION

This application claims priority to U.S. Provisional Patent Application No. 62/565,653, filed Sep. 29, 2017, which is incorporated by reference herein in its entirety.

TECHNICAL FIELD

Various embodiments concern techniques for diabetes management platforms.

BACKGROUND

Technological advances (e.g., improvements in processors, wireless communication, and packaging materials, in terms of their processing power, power consumption, and size) allow for new perspectives, paradigms, and possibilities. One such example is the development of wearable devices, where devices are worn on the body of the users rather than being separately carried and tracked by users. Further, by being on the person of the users, the wearable devices can provide new features and advantages previously unavailable to carried devices.

However, along with the new possibilities come various new challenges. For example, in integrating with users' daily lives and routines, the wearable devices can produce large amounts of data that may require contextual information surrounding the data. Without the contextual information, the produced data may lead to erroneous or partial results.

BRIEF DESCRIPTION OF THE DRAWINGS

Various features and characteristics of the present disclosure will become more apparent to those skilled in the art from a study of the Detailed Description in conjunction with the drawings. Embodiments of the present disclosure are illustrated by way of example and not limitation in the drawings, in which like references indicate similar elements.

Figure 1:
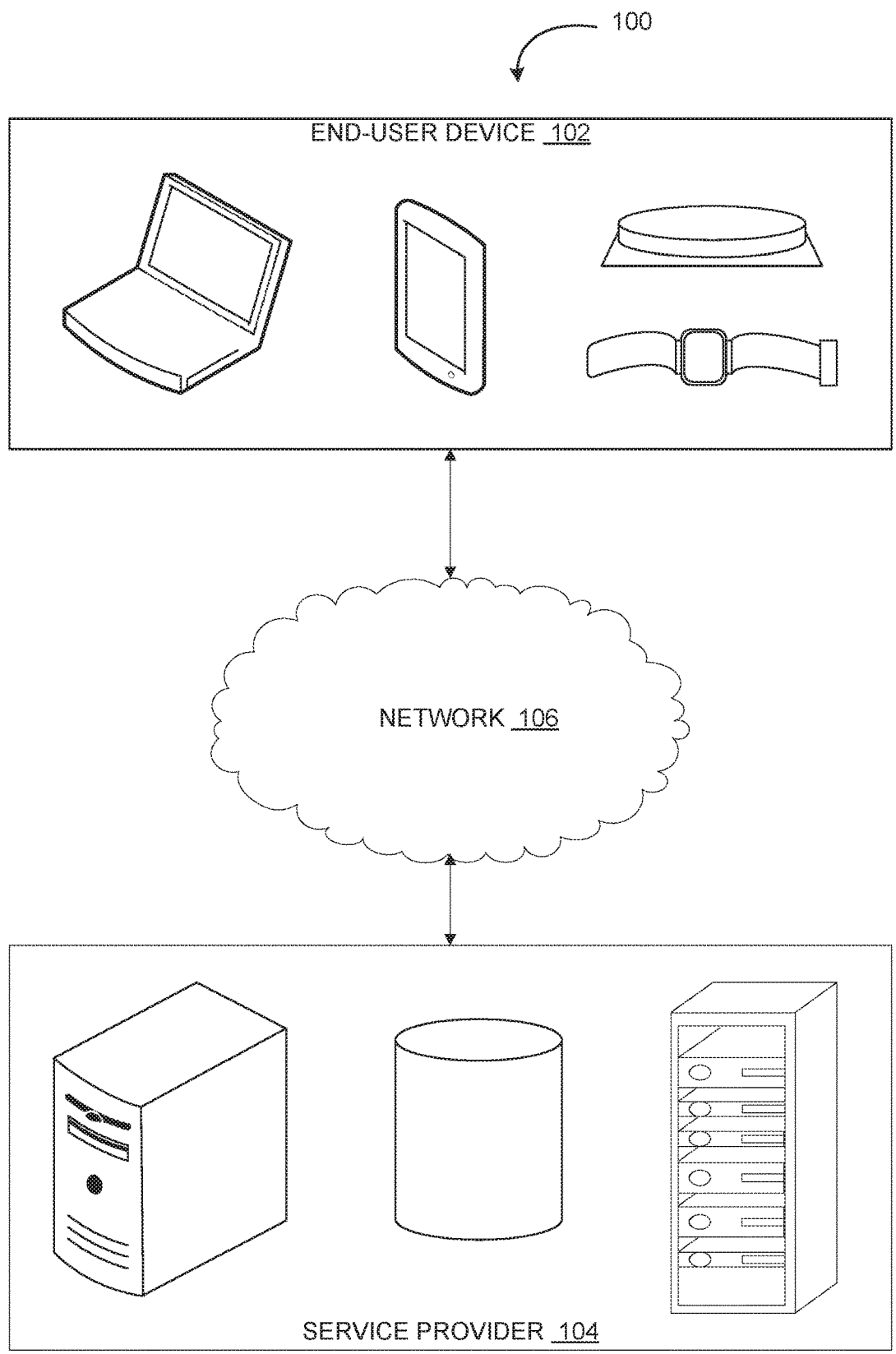
FIG. 1 illustrates an overview of a system in which some embodiments may operate.

The drawings depict various embodiments for the purpose of illustration only. Those skilled in the art will recognize that alternative embodiments may be employed without departing from the principles of the disclosed techniques. Accordingly, while specific embodiments are shown in the drawings, the disclosed techniques are amenable to various modifications.

DETAILED DESCRIPTION

Introduced here are techniques for organizing and presenting information, including contextual events, to a user through a device. The contextual events can include a condition experienced by the user or an action taken by the user that has an effect on a physiological state or condition, such as blood glucose level, of the user.

In some embodiments, the device (e.g., a mobile device, such as smart phones) can present various different types of information associated with the user's health, such as for managing diabetes. Diabetes is a disease in which a body's ability to produce or respond to the hormone insulin is impaired, resulting in abnormal metabolism of carbohydrates and elevated levels of glucose in the blood and urine. A technical signal indicative of the disease state of diabetes is blood glucose. However, blood glucose levels are affected by meal intake ("excursion"), body metabolism, and activity level. Accordingly, a healthcare professional or a patient cannot accurately interpret blood glucose levels without further insights to the contextual event (e.g., excursion, activity participation, medication intake, or other information) associated with such blood glucose levels.

One or more devices (e.g., a continuous glucose monitor ("CGM"), an activity tracker, a mobile device, a server or a service provider device, or a combination thereof) can detect and/or identify contextual events throughout the day for the user. For example, one or more devices can continuously monitor various aspects (e.g., health, such as for blood glucose levels and/or activity levels) and/or related information (e.g., meals or excursions, medication intake, activities, or exercise sessions) for a user. The system (e.g., using one or more devices therein) can identify the contextual events based on the gathered information since context involves concrete evidence of an environmental interaction that effectuates a change to the patient. The system can determine a time window (e.g., according to predetermined table including various possible events and corresponding time windows) associated with the determined contextual events. The time window can represent a delay duration (e.g., from an excursion to a rise/spike in the blood glucose levels) or an effectiveness duration (e.g., from a physical activity/exercise and a rise in metabolic levels) between the contextual events and its effect on the blood glucose level. Based on the determination, the system can use the time window to determine contextual relationships or connections to the user's health (e.g., levels and/or changes in CGM measurements).

To help the user manage their health (e.g., for managing diabetes), the system can present (e.g., display) information regarding the user's health, the associated contextual events, relationships or connections between the health information and the contextual events, or a combination thereof through one or more devices (e.g., a user's device or a healthcare professional's device). In presenting the contextual information, certain parameters or events can be highlighted (e.g., such as in response to the user's selection or interaction). For example, the device can present a CGM trace (e.g., a plot of the blood glucose levels or CGM readings corresponding to respective times of the CGM measurement). The system can receive a user indication for a timeframe or a portion on the CGM trace and present one or more contextual events and/or other related information associated with the selection. The system can also receive a user indication for a specific contextual event and present the corresponding CGM reading and/or other related information associated with the selection.

In some embodiments, the user can select (e.g., based on moving or locating a cursor, hovering the cursor at the location, clicking a button with the cursor at a location on the screen, dragging the cursor through a set of locations with the button pressed down, or physically touching one or more locations on the screen) a particular location on the CGM trace or a location under the trace. In response the user's selection, the device can highlight (e.g., by displaying or altering an image of) one or more icons representative of the contextual event associated with the time and/or the CGM reading selected by the user.

For example, the device can display the CGM trace along with a set of icons. The set of icons can each represent a contextual event (e.g., excursions, exercise sessions, or activities) that occurred along a timeline corresponding to the CGM trace. To reduce clutter within a display area (e.g., such as for smart phones or smart watches), the icons can be reduced in size, overlapped with each other, hidden and/or represented with alternative shapes (e.g., a marker on the CGM trace), etc. before or without the user indication. Based on or in response to the user's selection, the device can display the icon according to its full size/image (e.g., such as by enlarging the icon, bringing the icon in front of other icons, popping up the icons, scrolling the set of icons to place the corresponding icon under the selected time or at a center portion of the screen, or a combination thereof) corresponding to the selected time. For example, the device can display icons representing one or more of the context events that was determined as occurring at the selected time or that was determined to have occurred within a threshold duration from the selected time (e.g., for events known to have delayed effects on blood glucose levels, such as excursions or medicine intakes).

The set of icons can each represent a contextual event (e.g., excursions, exercise sessions, or activities) that occurred along a timeline corresponding to the CGM trace. To reduce clutter within a display area (e.g., such as for smart phones or smart watches), the icons can be reduced in size, overlapped with each other, hidden and/or represented with alternative shapes (e.g., a marker on the CGM trace), etc. before or without the user indication. Based on or in response to the user's selection, the device can display the icon according to its full size/image (e.g., such as by enlarging the icon, bringing the icon in front of other icons, popping up the icons, scrolling the set of icons to place the corresponding icon under the corresponding time or at a center portion of the screen, or a combination thereof) corresponding to the selected time. For example, the device can display icons representing one or more of the context events that was determined as occurring at the selected time or that was determined to have occurred within a threshold duration from the selected time (e.g., for events known to have delayed effects on blood glucose levels, such as excursions or medicine intakes).

In some embodiments, the device can display the CGM trace without the set of icons. Instead, the icons can be hidden and/or represented with alternative shapes (e.g., markers located on or overlapping the CGM trace at the time of occurrence) before or without the user indication. Based on or in response to the user's selection, the device can display the icon according to its full size/image, such as by revealing or displaying the icon, enlarging the icon, replacing the marker with the icon, popping or pulling the icon out of the marker, zooming in on the icon, or a combination thereof.

Along with the contextual event, the device can further display other related information in response to the selection. For example, the device can display the exact or estimated (e.g., such as using interpolations if no readings were taking at the selected time) CGM reading or level corresponding to the selection. Also for example, when the selection corresponds to an excursion, the device can display a type and/or an amount of food consumed for excursions, associated caloric information, or a combination thereof. Also for example, the device can display a time, a heart rate, a body temperature, ambient temperature, weather condition, a representation of an activity level (e.g., an estimate of burned calories, a step count, a heart rate, a duration or a rate of change thereof, or a combination thereof) for the corresponding context event or for a particular duration (e.g., from a reference time in a day, such as a wake-up time, from the previous excursion or medicine intake, or for a set time window).

In some embodiments, the device can represent a duration for the contextual event. For example, the device can display markers on the CGM trace and/or the timeline or time axis thereof. Also for example, the device can highlight the duration by placing markers for a beginning time and an ending time, by bolding a corresponding section of the trace, by overlaying a color on or changing the color of the corresponding section of the trace, by adjusting a display size or dimension of the corresponding icon, or a combination thereof.

Although some embodiments may be described using diabetes management, the disclosed techniques are generally implementation-agnostic. That is, various configurations discussed below can be utilized regardless of usage or application of the overall structure or device (e.g., for a carried device or a static/non-mobile device).

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context of the descriptions or examples herein clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling, either direct or indirect, between two or more elements. The coupling/connection can be physical, logical, or a combination thereof. For example, two devices may be communicatively coupled to one another despite not sharing a physical connection.

When used in reference to a list of multiple items, the word "or" is intended to cover all of the following interpretations: any of the items in the list, all of the items in the list, and any combination of items in the list.

Overall System

FIG. 1 an overview of a system (e.g., a computing system 100) in which some embodiments may operate. The computing system 100 can include a service provider device 104 (e.g., for a health service, an internet service provider, or a telecommunications or wireless communications service provider) connecting to and exchanging information with one or more end-user devices 102 through an external network 106. The service provider device 104 can include a circuit, a devices, a system, a function, or a combination thereof (e.g., servers) configured to identify contextual events and present user's health-related information in relation to the contextual events.

The end-user devices 102 can include one or more client computing devices (e.g., a wearable device, such as a mobile device, or a laptop). The end-user devices 102 may operate in a networked environment using logical connections to one or more remote computers. The end-user devices 102 can connect to each other, the service provider device 104, or a combination thereof. The end-user devices 102 can connect to other devices through the external network 106.

The external network 106 can include wired or wireless networks connecting various devices for communicating or exchanging data. For example, the external network 106 can include local area networks (LAN), wide area networks (WAN), wireless fidelity (WIFI) network, fiber optic networks, cellular network, the Internet, or a combination thereof.

One or more end-user devices 102, one or more service provider devices 104, or a combination thereof can identify contextual events and present user's health-related information accordingly. For example, one or more end-user devices 102 (e.g., the CGM and/or the activity monitor) can detect health-related information for the user. One or more end-user devices 102 (e.g., user's desktop or smartphone), one or more service provider devices 104, or a combination thereof can process the detected information to identify the contextual events. The computing system 100 can use one or more end-user devices 102 (e.g., user's desktop, smartphone, and/or smart watch) to present the user's health information along with the contextual events.

Figure 2A:
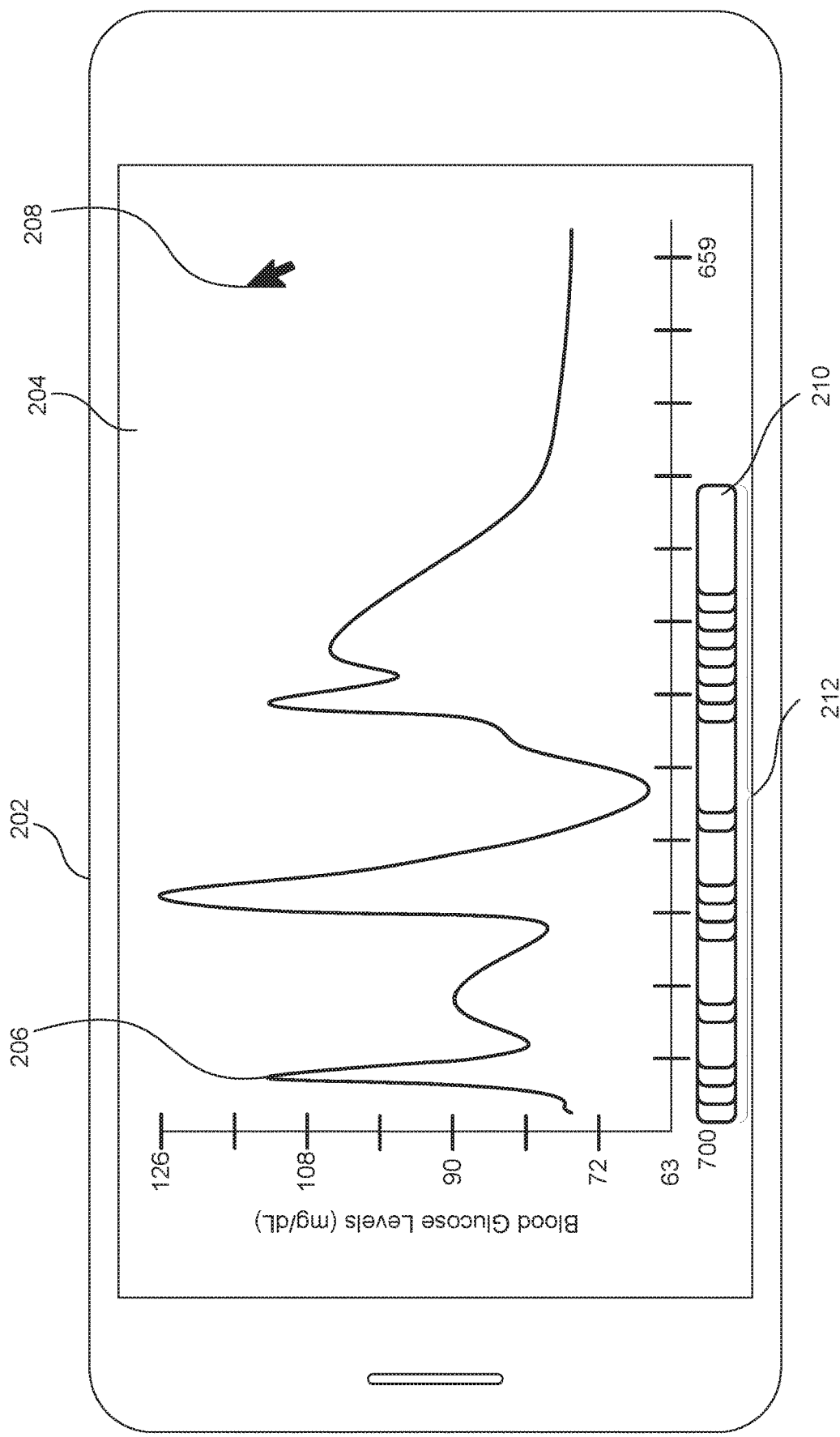
FIG. 2A and FIG. 2B illustrate a display of an electronic device according to some embodiments.
Figure 2B:
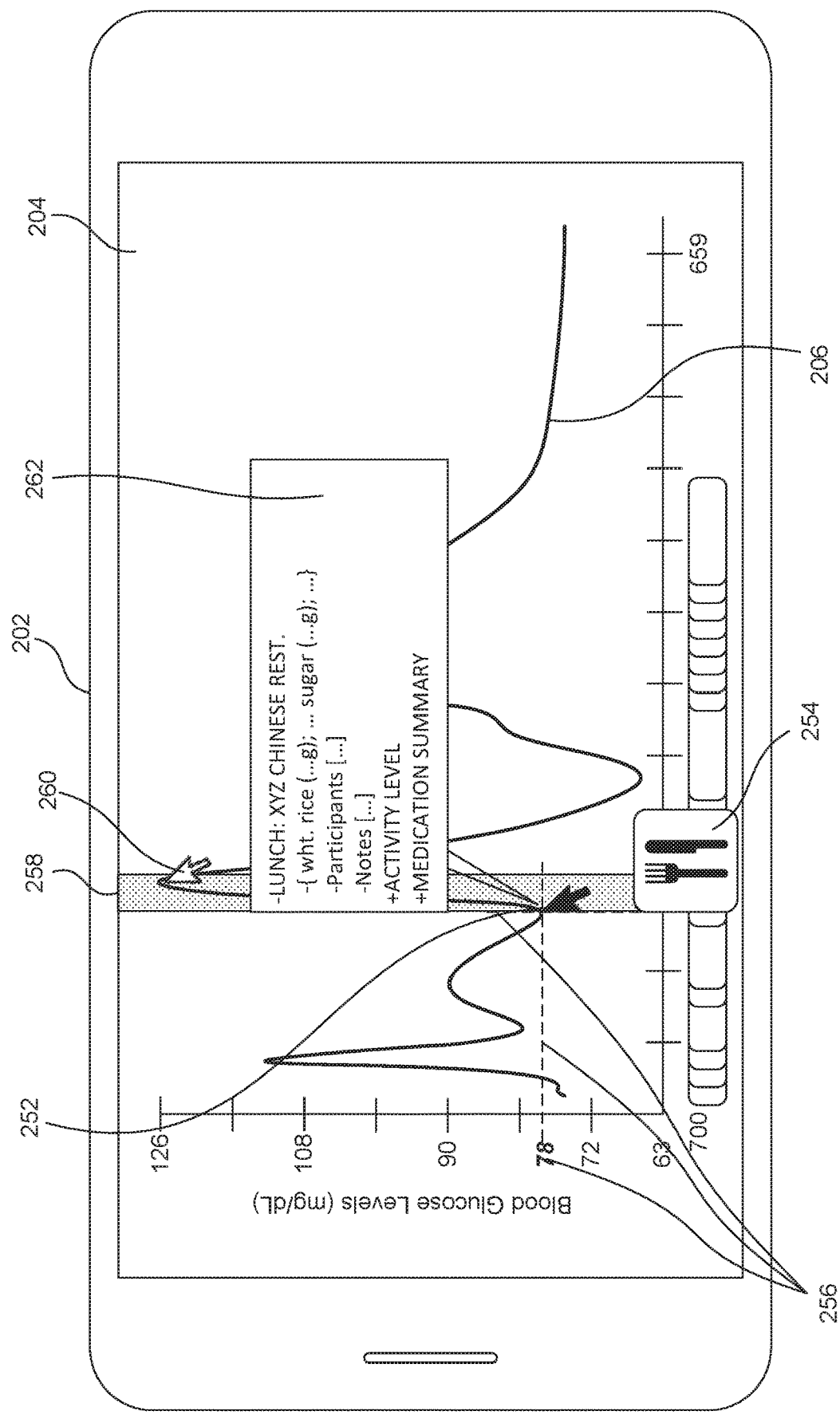

FIGS. 2A and 2B illustrate a display 204 of an electronic device 202 (e.g., one of the end-user devices 102 of FIG. 1) according to some embodiments. FIG. 2A illustrates a CGM trace 206 (e.g., measurement of blood glucose levels plotted across time, where a vertical axis represents a measurement value and a horizontal axis represents a time of the measurement) displayed on a display portion of a device before or without the user indication. In some embodiments, the electronic device can include or interact with a CGM to receive the blood glucose levels (e.g., CGM readings), and generate the CGM trace 206 based on the received information. In some embodiments, the electronic device can interact with a service provider's device (e.g., a server or a mainframe computer) that processes the CGM readings, and display the CGM trace 206 according to processed results.

The electronic device 202 can further communicate contextual events through the display using icons 210. Each of the icons 210 can represent a contextual event that has a significance or an impact on the blood glucose level. For example, contextual events can include exercise sessions, medicine intakes, excursions, etc. In some embodiments, such events can be logged by the user. In some embodiments, the electronic device 202 and/or the service provider device 104 can interact with other devices (e.g., a CGM, a heart rate monitor, an activity tracker, a calendar server, a Global Positioning System (GPS) device, a smart pill and/or a smart container, other user devices or sensors, or a combination thereof) to track the user's activities and/or status, and determine the contextual event from the tracking results.

Each of the icons 210 can be arranged or located in connection to the CGM trace 206, such as according to a time of occurrence. The occurrence time can be shown using the time axis of the CGM trace 206. As illustrated in FIG. 1A, time of both the CGM readings and the event occurrence can be represented along a horizontal time axis that represents a 24 hour day.

When the CGM trace 206 is displayed, a user indication can be made using a cursor 208 and/or a contact between the user's finger and the display surface. However, prior to or without the user indication (e.g., when the cursor 208 is located outside a threshold distance from the CGM or when the device has not detected user's touch for more than a threshold amount of time), the device can display an icon set 212 that have been minimized, overlapped, etc. Since the display is relatively small for some devices, such as for mobile devices or wearable devices, the device can focus on communicating the overall CGM trace 206 without presenting or focusing on the contextual events. For the contextual events, the device can use user indications as a cue to communicate the events that have relevance to selected portions of the CGM trace 206.

FIG. 2B illustrates the contextual event that is highlighted according to the user indication. When the computing system 100 of FIG. 1 (e.g., the end-user devices 102 and/or the service provider device 104 of FIG. 1) detects a user indication 252 (e.g., a cursor click, a cursor hover, or a contact between the user's finger and the display surface that is detected at or within a threshold distance from the CGM trace 206 or a particular icon), the electronic device 202 can highlight the corresponding counterpart. For example, when the user selects or indicates a portion of the CGM trace 206 (e.g., as illustrated in FIG. 2B), the electronic device 202 can display a highlighted icon 254 that corresponds to the selected portion of the CGM trace 206. Also for example, when the user indicates one of the icons 210 (e.g., the highlighted icon 254), the electronic device 202 can highlight corresponding portions 256 (e.g., dashed lines showing the level and/or time of the CGM measurement, the actual or estimated measurement value at the selected location of the CGM trace 206, etc.) of the CGM trace 206.

The computing system 100 can use a temporal correspondence 258 (e.g., a time-based relationship between certain events/user activities and blood glucose levels) between portions of the CGM trace 206 and the contextual event to identify and/or highlight the relevant information. In some embodiments, the temporal correspondence 258 can be based on contemporaneous occurrence (e.g., both are coincident along a vertical line). In some embodiments, the temporal correspondence 258 can be based on a known relationship between a type of the contextual event and a known or predetermined delayed or prolonged effect on the blood glucose level. For example, the computing system 100 can use predetermined or calculated reactionary delays and/or effective periods to associate excursions, exercises, and/or medicine intakes to non-contemporaneous portions of the CGM trace 206. Also for example, the computing system 100 can adjust or calculate the reactionary delays and/or the effective periods based on known or detected details of the event (e.g., a type and/or an amount of food that was consumed, an intensity level and/or a duration of the exercise, or a trait of medicine prescribed to taken by the user). Accordingly, the electronic device 202 can highlight a related event 260 that preceded a selected portion of the CGM trace 206 and/or highlight a portion of the CGM that occurs after the selected event 260.

Once the appropriate information is determined in according to the user indication and the temporal correspondence, the computing system 100 can use a variety of methods to highlight the information that corresponds to the user indication. In some embodiments, the computing system 100 can highlight the icons by displaying the highlighted icon 254 according to its full size/image (e.g., such as by enlarging the icon, bringing the highlighted icon 254 in front of other icons, showing or darkening image within the highlighted icon 254, popping up the highlighted icon 254, scrolling the icon set 212 to place the target icon under the selected time or at a center portion of the screen, or a combination thereof). In doing so, the computing system 100 can distinguish the highlighted icon 254 from other icons in the icon set 212. In some embodiments, the computing system 100 can highlight portions of the CGM trace 206 by displaying a time and/or the CGM reading for the portions 256 corresponding to the user indication (e.g., such as for displaying 'x' and 'y' coordinates on a plot), using horizontal and/or vertical lines coincident with the user indication or the cursor 208, placing a marker on the CGM trace 206, changing the color or bolding at the corresponding portion of the CGM trace 206, or a combination thereof.

In some embodiments, the electronic device 202 can further communicate other information related to the contextual event, such as event details. For example, the electronic device 202 can communicate a geographic location of the contextual event. Also for example, the electronic device 202 can communicate related details 262 regarding names, types, amounts, and/or nutritional information regarding consumed food for excursion events. Also for example, the electronic device 202 can communicate the related details 262 regarding names, types, intensity, and/or durations for exercise or physical activity sessions. Also for example, the electronic device 202 can communicate a running total (e.g., a total calculated between the selected time and a reference time, such as for an up to the moment tally for each day) of health-related metrics, such as total calories consumed or burned, total amount of medication taken, total number of steps, etc. Also for example, the related details 262 can include links to other related contextual events.

In some embodiments, the electronic device 202 can communicate the related details 262 based on an image within the icon. For example, the electronic device 202 can display a generic image (e.g., illustrated as a fork and a knife in FIG. 1B) for the icon before the user indication and/or without the details. Based on a cue (e.g., a further input from user or a computing state), the electronic device 202 can replace the generic image with a specific image (e.g., an image representing the consumed food, an image representing the activity, or a name or trademark of the medicine) or display the specific image in addition to the generic image (e.g., as an additional icon) to communicate the details of the contextual event.

Figure 3A:
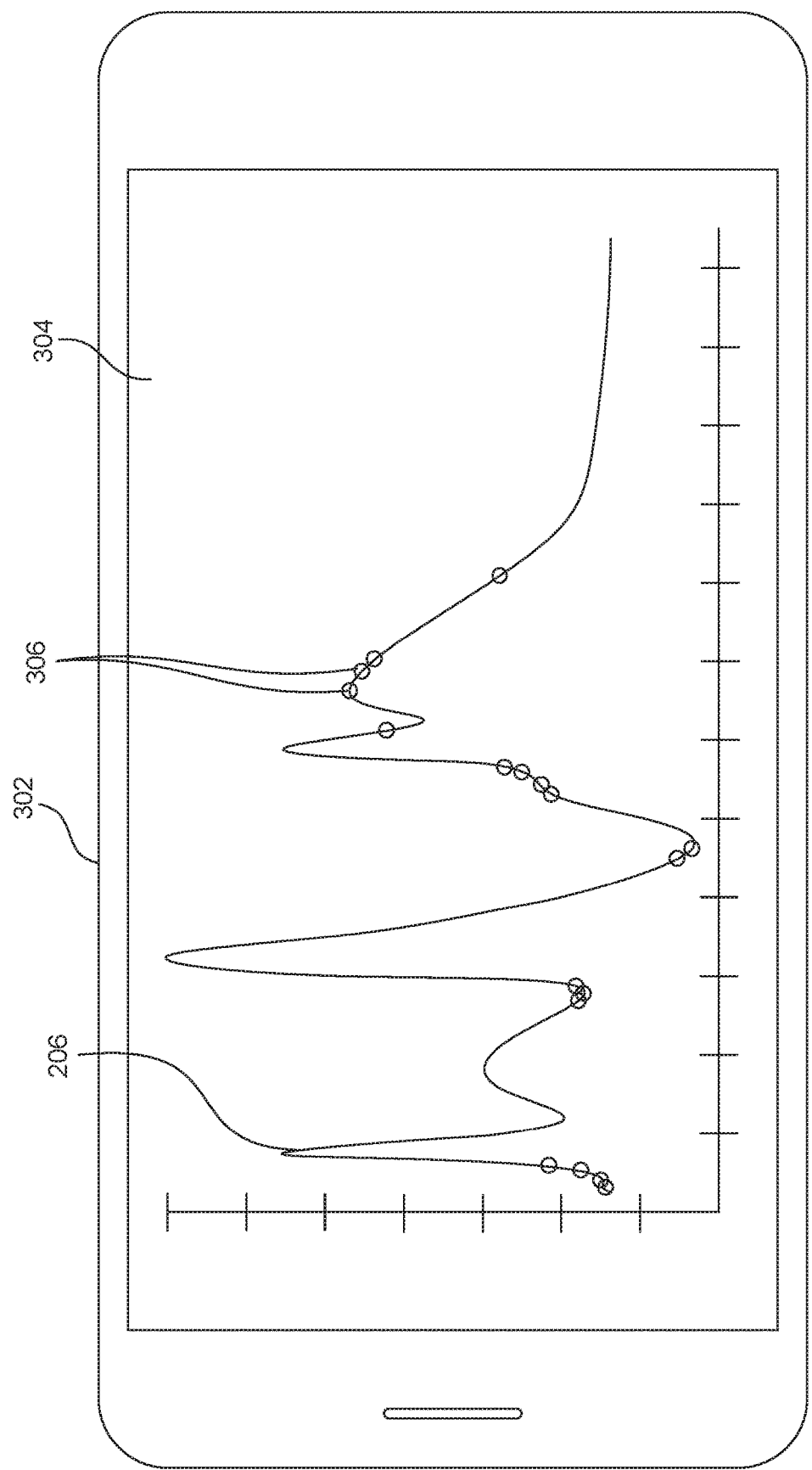
FIG. 3A and FIG. 3B illustrate a display of an electronic device according to some embodiments.
Figure 3B:
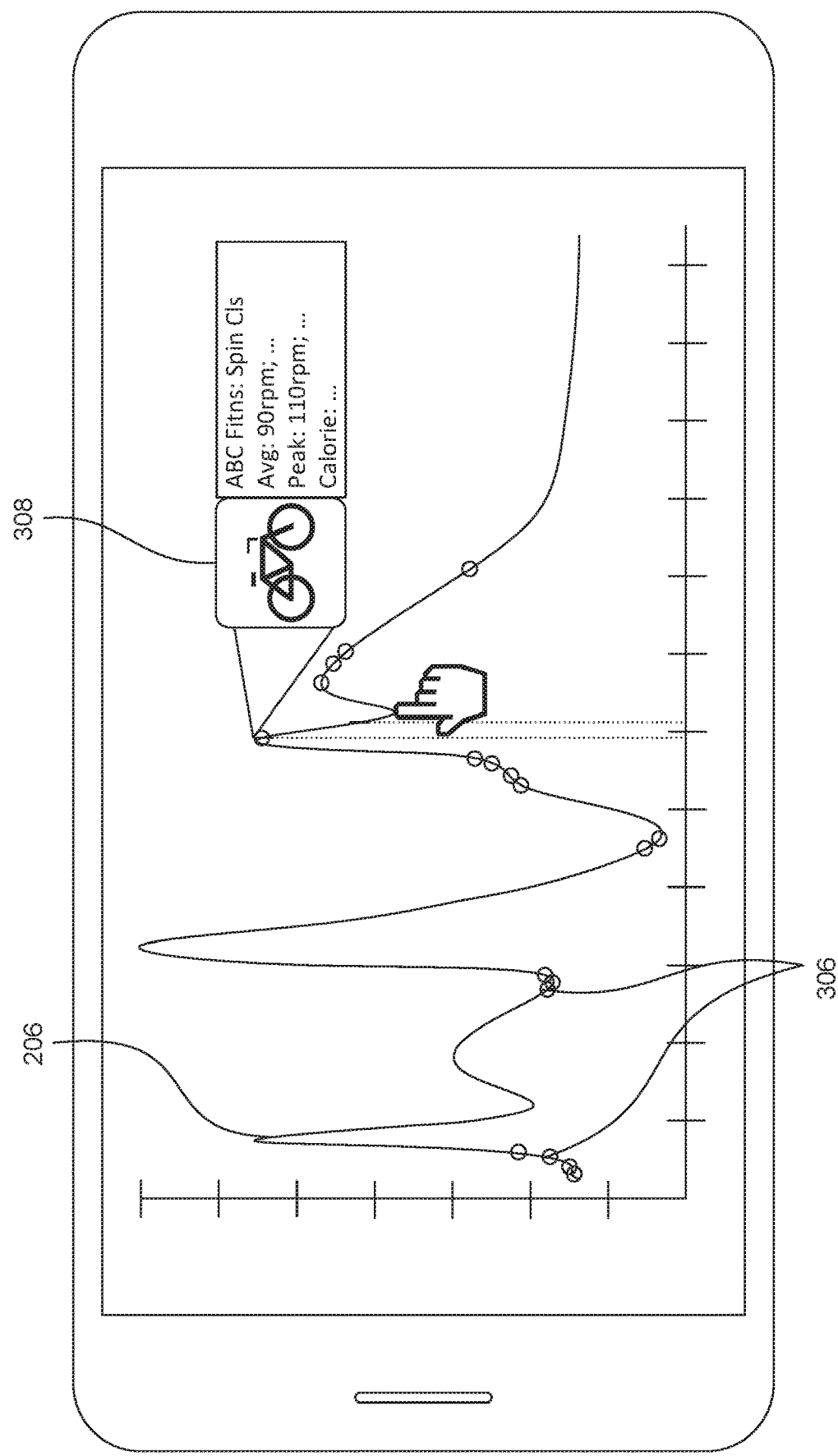

FIG. 3A and FIG. 3B illustrate a display 304 of an electronic device 302 (e.g., one of the end-user devices 102 of FIG. 1) according to some embodiments. In some embodiments, such as illustrated in FIG. 3A and in contrast to FIGS. 2A and 2B, the electronic device 302 can initially (e.g., before or without the user indication) communicate the CGM trace 206 without the icons (e.g., the icons 210 of FIG. 2A and FIG. 2B). In some embodiments, the icons can be replaced by or reshaped/resized as markers 306 that represent the corresponding contextual events. The markers can be located directly on or overlapping the CGM trace 206 according to the occurrence time of the contextual event.

FIG. 3B illustrates the contextual event highlighted according to the user indication. When the computing system 100 of FIG. 1 (e.g., the end-user devices 102 and/or the service provider device 104 of FIG. 1) detects the user indication, the electronic device 302 can highlight the corresponding counterpart. The electronic device 302 can highlight by displaying a corresponding icon 308 (e.g., expanded or full size/view icon) from or based on the markers 306 (e.g., instead of the icon set 212 in FIG. 2A or FIG. 2B). For example, the electronic device 302 can highlight the contextual event associated with the user indication by displaying or popping up the related icon 308 in addition to the marker, expanding the marker to a full view or state of the icon, replacing the marker with the icon, etc.

Example Operation

Figure 4:
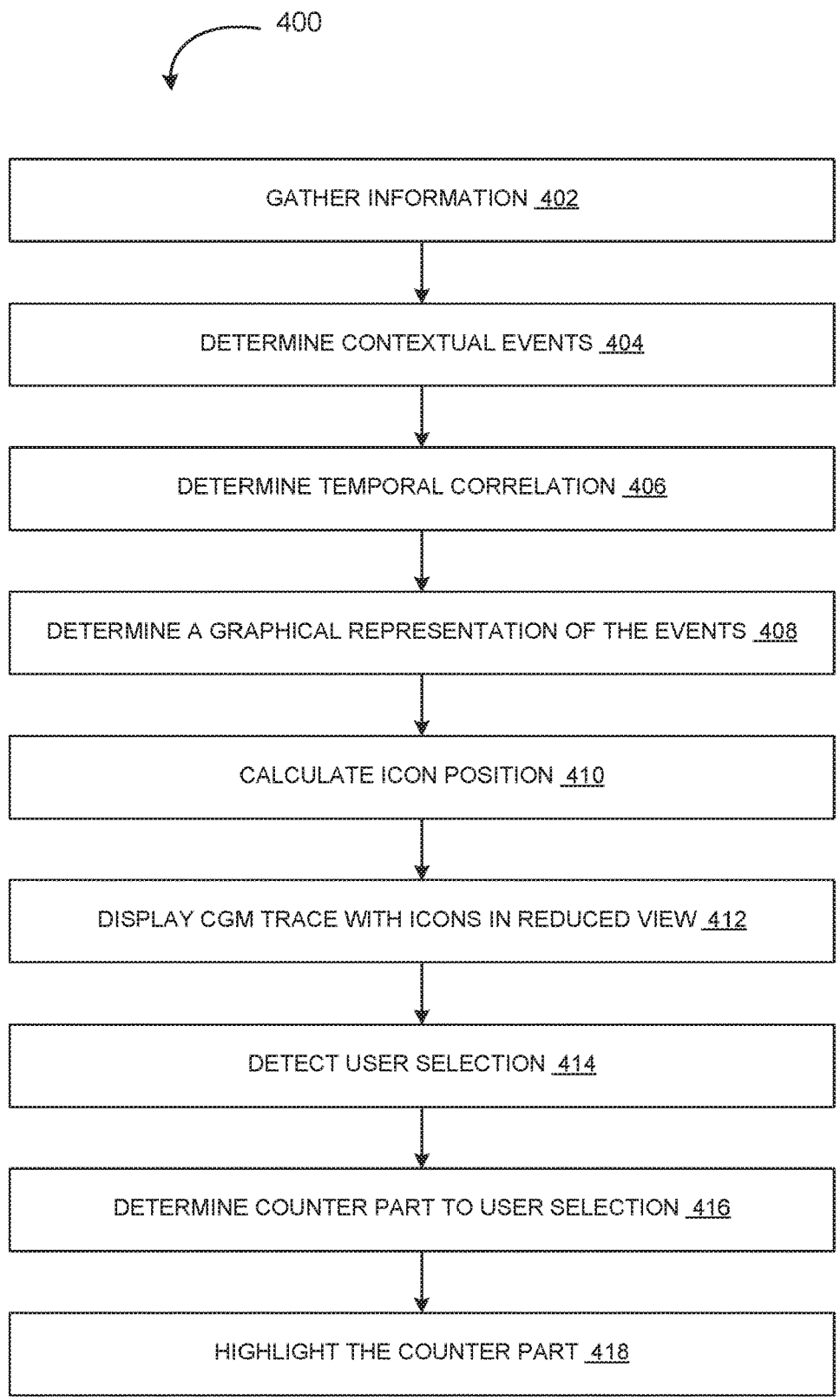
FIG. 4 illustrates an example method of operating the electronic device according to some embodiments.

FIG. 4 illustrates an example method 400 of operating the computing system 100 of FIG. 1 (e.g., the end-user devices 102 and/or the service provider device 104 of FIG. 1) according to some embodiments. At block 402, the computing system 100 can gather information (e.g., a status, a condition, an action, a location, a schedule or a calendar, healthcare-related data, or a combination thereof) from one or more data channels (e.g., streaming channels and/or asynchronous/discrete channels, such as user-initiated reports through web portal, user-initiated reports through mobile app, mobile app reported sensor streams, wearable devices (CGM), healthcare platform systems such as pharmacy systems, hospital systems, etc.). The computing system 100 can gather information that describe or correspond to a user or a patient profile. For example, one or more devices (e.g., a CGM, an activity tracker, a smart phone, a wearable device, a mobile device, a GPS device, devices belonging to or operated by other users, or a combination thereof) can sense the information regarding the user. Also for example, one or more devices (e.g., a server, a smart phone or watch, a device designated by the user, or a combination thereof) can receive the information from other sensing devices. The information can include the CGM readings and their measuring times and/or the CGM trace 206 of FIG. 2.

At block 404, the computing system 100 can determine the contextual events (e.g., indications of a patient activity that has a potential of affecting metabolism of the patient) based on the gathered information. For example, one or more devices (e.g., the end-user devices 102 and/or the service provider device 104) can use the gathered information to determine excursions, exercise sessions, activities, medicine intakes, or a combination thereof performed by the user. In some embodiments, the one or more devices can use templates and/or machine learning (e.g., cluster analysis, neural networks, etc.) to determine the contextual events from the gathered information. For example, the computing system 100 can determine an excursion based on user's location data (e.g., GPS coordinates) relative to location of known restaurants or kitchens, a spike or a rise in the CGM readings (e.g., indicating a preceding excursion), predetermined time windows (e.g., traditional meal times or based on user-specific patterns) indicating increased likelihood of excursions, accelerometer readings indicating patterns of movements associated with eating (e.g., repeated hand-to-face movements, generally stationary and/or seated posture, etc.), user's schedule calendar user input identifying or verifying an excursion, or a combination thereof.

At block 406, the computing system 100 can determine the temporal correlation 258 (e.g., a time window corresponding to the contextual event) between the contextual events and the CGM trace 206 or portions thereof. The one or more devices can determine the temporal correlation 258 according to the determined contextual events and/or the gathered information associated with the contextual events. In some embodiments, the one or more devices can use a formula, a template, a table, a value, or a combination thereof that is predetermined for describing a duration and/or an amount of influence that various contextual events have on the blood glucose levels. In some embodiments, the one or more devices can use machine learning models to identify the temporal correlation between the CGM readings and the contextual events.

At block 408, the computing system 100 can determine a graphical representation (e.g., the icon 210 of FIG. 2) of the contextual event. For example, using one or more devices (e.g., the end-user devices 102 and/or the service provider device 104, such as a cloud device), the computing system 100 can select the icons 210 corresponding to the contextual events (e.g., according to a predetermined set that ties specific icons to various events or their categories). Also for example, the one or more devices can use as the icon 210 a received image (e.g., an upload from the user) having an association with the contextual event (e.g., photo of the user's meal). In some embodiments, the graphical representation can include vertical and/or horizontal lines that correspond to the blood glucose level reading/estimate, a pop-up or a highlight of the actual or estimated blood glucose level, a portion of the CGM trace, a text description, an arrow or a cursor, etc.

The one or more devices can select the icons 210 according to the determined contextual events and/or the gathered parameters (e.g., determined excursion and/or the food consumed by the user). For example, the one or more devices can select the icons 210 according to a predetermined table or a user-defined table describing connections between various available icons and the contextual events and/or the gathered parameters matching each of the available icons.

Also for determining the graphical representation, the one or more devices can calculate a display format for the icons 210. For example, the one or more devices can calculate a dimension, a representation or an alternate view, or a combination thereof for presenting the icons 210 in multiple different views (e.g., a full-view or a reduced view, such as a smaller or hidden view of the icons for displays under a predetermined size limit or for mobile devices). Also for example, as represented at block 410, the one or more devices can calculate the display positions of the icons 210 according to occurrence time of the contextual event (e.g., such as in relative order amongst the icons and/or in relation to the time represented on the CGM trace 206), the time window, or a combination thereof.

At block 412, the computing system can display the CGM trace 206 along with the determined icons in a reduced format. For example, the icons can be reduced in size or replaced with representations as illustrated in FIGS. 2A and 3A and discussed above. The system (e.g., in the cloud and/or using the user's device) can generate and display the CGM trace 206 over or across time, and further display the icons in the reduced view according to the calculated icon positions.

At block 414, the computing system 100 can detect a user indication. The one or more devices (e.g., in the cloud and/or using the user's device) can use an input-output interface or a graphical user interface (GUI) control device (e.g., a touch screen, a motion sensor, a microphone, or a combination thereof) to detect the user's interest in a time point along the graph of the blood glucose level (e.g., a portion of the CGM trace 206, one of the icons, or a combination thereof).

At block 416, the computing system 100 can determine a counterpart to the user indication. The one or more devices (e.g., in the cloud and/or using the user's device) can identify the icon/contextual event or the CGM readings having the time window overlapping or including the time point corresponding to the user interest. For example, the computing system 100 can determine the counterpart as one or more of the icons that are associated with contextual events having effective durations overlapping or contemporaneous with the user-selected portion of the CGM trace 206. Also for example, the computing system 100 can determine the counterpart as a portion of the CGM trace 206 that is contemporaneous with or overlaps the contextual event associated with the user-selected the icon(s). Further the system can determine a specific icon or a specific portion based on a time corresponding to the user indication, the corresponding contextual event, and the temporal correlation associated with the corresponding contextual event.

At block 418, the computing system 100 can highlight the counterpart (e.g., in a display) in response to the user indication. For example, the one or more devices (e.g., in the cloud and/or using the user's device) can determine and display a full-view of the appropriate icon (e.g., using one or more of the ways discussed above) and/or move the corresponding icon to a center portion or a designated portion of the display to distinguish it from other icons (e.g., remaining in the reduced view, overlapped by other icons, etc.). Also for example, the one or more devices can highlight the portion of the CGM (e.g., based on communicating the CGM reading, a color or a line size, a time duration, or a combination thereof, such as discussed above).

Determining the contextual event associated with the user's health information specifically improves accuracy in assessing the user's health conditions. For example, the computing system 100 can determine the lifestyle events or choices of the user that contribute to the user's health conditions, such as user's blood glucose levels throughout the day. In addition to reporting the blood glucose levels, the contextual events can provide potential causes to issues and/or corrections to eliminate or improve any health issues. Further, based on determining the contextual events, the computing system 100 can provide remedial actions in real-time (e.g., a change or an update in the next medicine intake time or dosage) and/or trends or patterns (e.g., for particular user's tendencies, such as reactions to stress or seasonal behaviors, or across multiple users) that can assist the user and/or healthcare professionals in managing the user's health conditions.

Using the computing system 100 to determine the contextual event (e.g., an excursion, a particular activity, or an exercise session) based on information gathered from various devices (e.g., smartphone, CGM, and/or activity tracker) and further calculate an effective time window (e.g., the duration that the determined event impacts or affects the user's blood glucose levels) based on the information and/or the determined event provides improved accuracy and usability. The computing system 100 can determine the contextual events with or without user inputs to improve the usability and the accuracy. Further, the computing system 100 can store any details that the user provides (e.g., user's mood, details about the amount or the dish consumed during excursion, or specific exercises or activities performed by the user) with the relevant CGM readings/trace portions. At a later time or for a different user, the computing system 100 can analyze and use the stored information (e.g., using machine learning or pattern recognition) to recognize and provide the previously provided details for matching patterns in the CGM readings/traces.

Presenting the contextual event along with the user's health information according to a connection or a relationship between the events and the user's health specifically improves usability. The contextual events can be linked to various portions of the CGM readings and can be displayed (e.g., through a graphical user interface using specifically structured interface formats as illustrated above) based on user interactions as discussed above. Based on the link between the contextual events and the CGM readings (e.g., based on the time window), the computing system 100 can arrange and display the contextual events, which can be numerous throughout a user's day, to present the events relevant to the user's selection. As such, the computing system 100 can quickly present information (e.g., the contextual events, the CGM levels, and/or the time window) that may be of interest to the user, thereby alleviating the user from search through the potentially numerous events. Further, the improvement in the usability is further highlighted when the information is presented in most mobile devices (e.g., smartphones, smart glasses, or smart watches) due the limited screen size of such devices.

Figure 5:
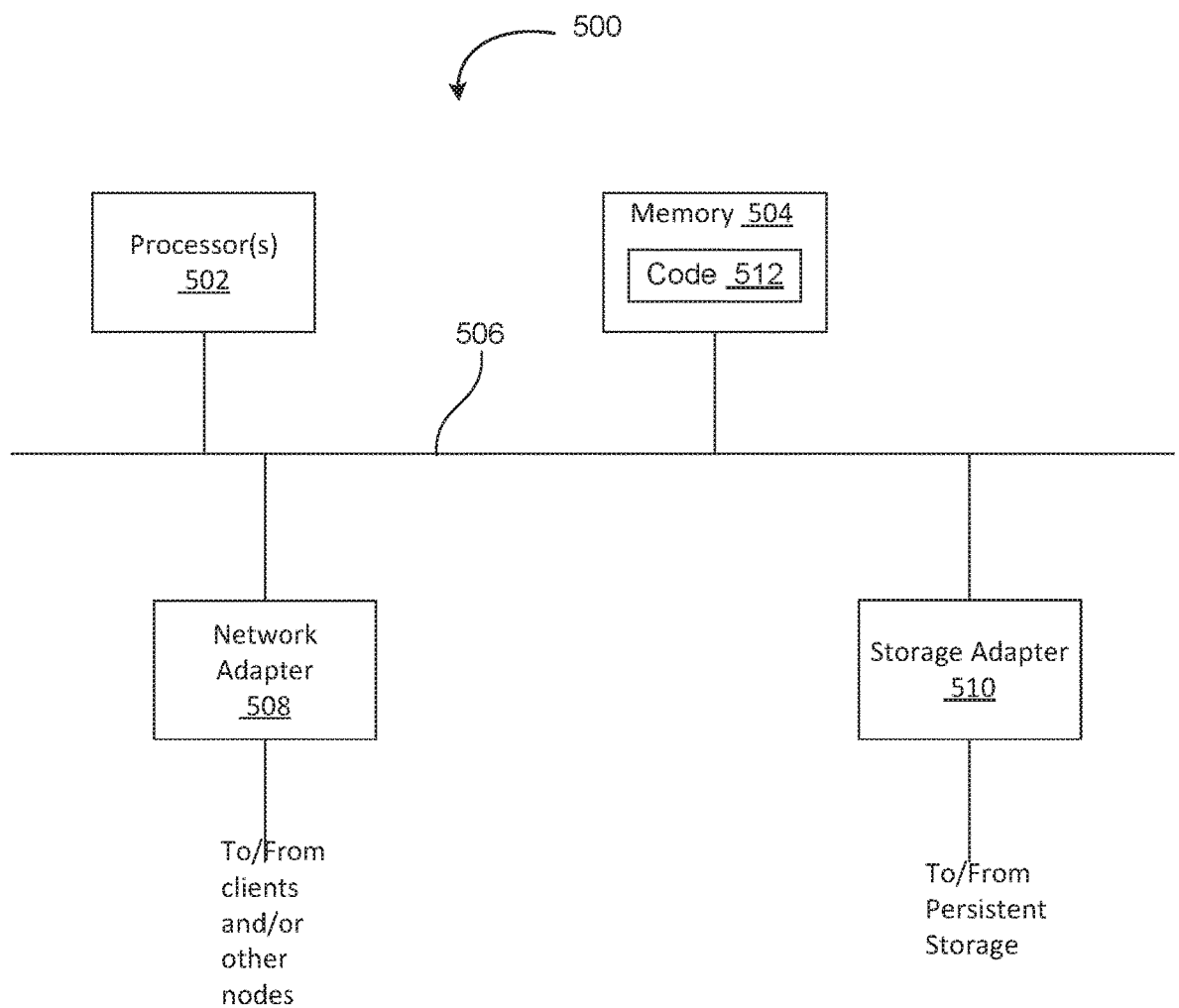
FIG. 5 is a block diagram of an example of a computing device, which may represent one or more computing devices or servers described herein, in accordance with various embodiments.

FIG. 5 is a block diagram of an example of a computing device 500 (e.g., the end-user devices 102 of FIG. 1 and/or the service provider device 104 of FIG. 1), which may represent one or more computing devices or servers described herein, in accordance with various embodiments. The computing device 500 can include one or more computing devices that implement the computing system 100 of FIG. 1. The computing device 500 can execute at least part of the method of FIG. 4. The computing device 500 includes one or more processors 502 and memory 504 coupled to an interconnect 506. The interconnect 506 is an abstraction that represents any one or more separate physical buses, point-to-point connections, or both connected by appropriate bridges, adapters, or controllers. The interconnect 506, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire". The interconnect 506 can also include wireless connection or communications between components.

The processor(s) 502 is/are the central processing unit (CPU) of the computing device 500 and thus controls the overall operation of the computing device 500. In certain embodiments, the processor(s) 502 accomplishes this by executing software or firmware stored in memory. The processor(s) 502 may be, or may include, one or more programmable general-purpose or special-purpose microprocessors, digital signal processors (DSPs), programmable controllers, application specific integrated circuits (ASICs), programmable logic devices (PLDs), trusted platform modules (TPMs), or the like, or a combination of such devices.

The memory 504 is or includes the main memory of the computing device 500. The memory 504 represents any form of random access memory (RAM), read-only memory (ROM), flash memory, or the like, or a combination of such devices. In use, the memory 504 may contain a code 512 containing instructions according to the operation of at least a portion of the computing system 100 or the method disclosed herein.

Also connected to the processor(s) 502 through the interconnect are a network adapter 508 and a storage adapter 510. The network adapter 508 provides the computing device 500 with the ability to communicate with remote devices, over a network and may be, for example, an Ethernet adapter, Fiber Channel adapter, or a wireless modem. The network adapter 508 may also provide the computing device 500 with the ability to communicate with other computers. The storage adapter 510 enables the computing device 500 to access a persistent storage, and may be, for example, a Fiber Channel adapter or SCSI adapter.

The code 512 stored in memory 504 may be implemented as software and/or firmware to program the processor(s) 502 to carry out actions described above. In certain embodiments, such software or firmware may be initially provided to the computing device 500 by downloading it from a remote system through the computing device 500 (e.g., via network adapter).

The techniques introduced herein can be implemented by, for example, programmable circuitry (e.g., one or more microprocessors) programmed with software and/or firmware, or entirely in special-purpose hardwired circuitry, or in a combination of such forms. Special-purpose hardwired circuitry may be in the form of, for example, one or more application-specific integrated circuits (ASICs), programmable logic devices (PLDs), field-programmable gate arrays (FPGAs), etc.

Software or firmware for use in implementing the techniques introduced here may be stored on a machine-readable storage medium and may be executed by one or more general-purpose or special-purpose programmable microprocessors. A "machine-readable storage medium," as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible storage medium includes recordable/non-recordable media (e.g., read-only memory (ROM); random access memory (RAM); magnetic disk storage media; and/or optical storage media; flash memory devices), etc.

The term "logic," as used herein, can include, for example, programmable circuitry programmed with specific software and/or firmware, special-purpose hardwired circuitry, or a combination thereof.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the presented techniques can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the presented techniques with which that terminology is associated. In general, the terms used in the following claims should not be construed to limit the presented techniques to the specific embodiments disclosed in the specification, unless those terms are explicitly defined herein. Accordingly, the actual scope of the presented techniques encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the presented techniques be limited not by this Detailed Description, but rather by any claims that issue on an application based hereon. Accordingly, the disclosure of various embodiments is intended to be illustrative, but not limiting, of the scope of the presented techniques as set forth in the following examples.

I claim:

1. A method comprising:
receiving healthcare-related data from a plurality of data streams associated with a profile of a patient, wherein the plurality of data streams includes a data channel from a wearable device providing at least a portion of the healthcare-related data through a day of the patient;
determining a set of contextual events at least partially based on the data channel,
wherein each contextual event includes details representative of a type, an amount, a content, an intensity, a duration, or a combination thereof for a patient activity that impacts a blood glucose level of the patient, and
wherein the set of contextual events includes at least a first event and a second event that respectively occurred at a first time and a second time;
identifying, based on the set of contextual events, a first time window and a second time window respectively corresponding to the first event and the second event, wherein each of the first and second time windows represents an effectiveness duration of the corresponding event on the blood glucose level of the patient, wherein the effectiveness duration is calculated or adjusted according to the details of the corresponding contextual event;
determining a first graphical representation and a second graphical representation for the first event and the second event;
generating a graph of the blood glucose level of the patient over a continuous duration of time for display;
displaying on a display one or more representations of the set of the contextual events and the graph of the blood glucose level;
detecting, based on an output of a GUI control device, a user indication of a time point corresponding to a user-selected portion of the displayed graph of the blood glucose level, wherein the time point is representative of a discrete moment in time experienced by the user and occurring after the first time and the second time; and
highlighting, in the display, the first and second graphical representations when the first and second time windows overlap the time point,
wherein the first and second time windows overlap each other at least at the time point according to corresponding calculated or adjusted effectiveness durations, and
wherein the highlighted first and second graphical representations are visually distinguished in comparison to the one or more representations for the set of contextual events, wherein the highlighted first and second graphical representations the first and second events having direct cumulative effects on the blood glucose level of the patient at the detected time point while reducing or distinguishing from clutter on the display.

2. The method of claim 1, wherein:
the user indication represents a user selection received via a touch screen;
highlighting the first and second graphical representations includes:
displaying a first view for representing the set of contextual events prior to said highlighting, wherein the first view provides less information in comparison to a second view; and
displaying the second view for presenting each of the first and second events in response to said detecting the user indication, wherein the second view is a full view of the first and second graphical representations for the touch screen.

3. The method of claim 2, wherein:
displaying the first view includes displaying summary icons corresponding to the first and second graphical representations among a set of selectable graphical representations representative of the set of contextual events associated with the profile, wherein, when unselected, the first and second graphical representation are displayed as the summary icons that are smaller than the first and second graphical representations; and
displaying the second view includes displaying a full-view of the first and second graphical representations.

4. The method of claim 3, further comprising:
displaying the graph of blood glucose level; and
wherein:
displaying the first view includes displaying the summary icons directly on or directly over the graph according to occurrence times of the first and second events; and
displaying the second view includes displaying the full-view of the first and second graphical representations over or replacing the summary icons or displaying the full-view of each of the first and second graphical representations at corresponding locations.

5. The method of claim 3, wherein:
displaying the first view includes displaying the summary icons at least partially overlapped under the selectable graphical representations within the set; and
displaying the second view includes displaying the full-view of the first and second graphical representations in front of the set of selectable graphical representations, displaying the full-view of the first and second graphical representations based on transitioning from the summary icons for a pop-up display, or a combination thereof.

6. The method of claim 1, further comprising communicating detailed information in response to the user indication, wherein the detailed information includes a blood glucose reading, a number of steps, a calorie count, a menu item, an activity level, a representation thereof, or a combination thereof.

7. The method of claim 2, further comprising:
displaying the blood glucose trace;
wherein highlighting the graphical representation includes:
displaying the first view includes displaying a set of selectable graphical representations representative of the set of contextual events associated with the profile, wherein the set of selectable graphical representations is vertically offset from the blood glucose trace; and
displaying the second view includes moving items within the set of selectable graphical representations for scrolling through the set.

8. An electronic system comprising:
one or more processors configured to:
receive healthcare-related data from one or more data streams associated with a profile of a patient, wherein the plurality of data streams includes a data channel from a wearable device providing at least a portion of the healthcare-related data through a day of the patient;

control a display to show a graph of a blood glucose level of the patient over a continuous duration based on data provided by the wearable device;

receive a user indication of a time point corresponding to a user-selected portion of the displayed graph of the blood glucose level, wherein the user indication corresponds to a discrete moment in time experienced by the user and occurs after the first time and the second time;

determine two or more events and corresponding details at least partially based on the healthcare-related data, wherein each of the two or more events is associated with an event time, and the details represent a type, an amount, a content, an intensity, a duration, or a combination thereof for a patient activity that impacts a blood glucose level of the patient;

identify a time window for each of the two or more events according to the corresponding details, wherein:
the time window represents an effectiveness duration of the corresponding event on the blood glucose level of the patient,
the identified time window overlaps the user-selected time point,
identified windows for the two or more events overlap each other at least at the user-selected time point;

determine a graphical representation for each of the two or more events, wherein the graphical representation includes a first view and a second view for visually presenting the corresponding event on a display, wherein:
the first view is configured to present the corresponding event in a same format as other events, and
the second view is configured to highlight the corresponding event in response to a user indication detected based on an output of a GUI control device, wherein the user indication corresponds to a time point within the corresponding time window; and a communication circuit, operably coupled to the one or more processors, configured to communicate one or more signals for transitioning graphical representations of the two or more events from the first view to the second view for highlighting the two or more events having direct cumulative effects on the blood glucose level of the patient at the user-selected time point while reducing or distinguishing from clutter on the display.

9. The system of claim 8, wherein the communication circuit includes a modem circuit configured to transmit the graphical representations to a display.

10. The system of claim 8, wherein:
the one or more processors is/are configured to:
generate a graph of the blood glucose level of the patient over time for display, and
detect, based on an output of a GUI control device, the user indication associated with a time point along the graph of the blood glucose level; and
the communication circuit includes a display configured to:
display the first view before or without the user indication, and display the second view in response to the user indication when the time point is within the time windows of the two or more events.

11. The system of claim 8, wherein:
the first view includes summary icons of among a set of selectable graphical representations representative of the two or more events associated with the profile, wherein, when unselected, the summary icons are smaller than the second view; and
the second view includes a full-view of the graphical representations for the two or more events.

12. The system of claim 11, wherein the one or more processors is/are configured to:
generate a graph of the blood glucose level over time for display; and
wherein:
the first view includes the summary icons displayed directly on or over the graph according to event times of the two or more event; and
the second view includes the full-view of the graphical representations displayed over or replacing the summary icons or at locations associated with the summary icons.

13. The system of claim 11, wherein:
the first view includes the summary icons at least partially overlapped under the selectable graphical representations within the set; and
the second view includes the full-view of the graphical representations displayed in front of the set of selectable graphical representations, the full-view of the graphical representations displayed based on transitioning from the summary icon for a pop-up display, or a combination thereof.

14. The system of claim 8, wherein the communication circuit is configured to communicate detailed information in response to the user indication, wherein the detailed information includes a blood glucose reading, a number of steps, a calorie count, a menu item, an activity level, a representation thereof, or a combination thereof.

15. A health-monitoring system comprising:
a display configured to:
display a graph of patient blood glucose levels over a continuous duration as provided by a wearable device of a patient;
display graphical representations of contextual events, wherein the contextual events (1) are each indicative of a patient activity that occurred at an event time and has a potential of affecting patient metabolism and (2) each corresponds to a time window representative of an effectiveness duration of the corresponding contextual event on the blood glucose level of the patient; and
highlight two or more representations based on a user indication; and
one or more processors operably coupled to the communication circuit, configured to:
receive healthcare-related data from a plurality of data streams associated with a profile of the patient, wherein the plurality of data streams includes a data channel from the wearable device providing the blood glucose levels of the patient through a day;
calculate or adjust the time window for each of the contextual events according to details of the contextual events as indicated by the healthcare-related data, wherein the details represent of a type, an amount, a content, an intensity, a duration, or a combination thereof for the contextual event having an effect on the blood glucose level of the patient;

detect the user indication associated with a time point corresponding to a user-selected portion of the displayed graph, wherein the time point is representative of a discrete moment in time experienced by a user; and update the display for highlighting the two or more representations in response to the user indication when the time point is after the event times and within time windows of events corresponding to the two or more representations, wherein the time windows of the events corresponding to the two or more representations overlap at least at the time point, and wherein the display is updated for communicating to the user the contextual events having direct cumulative effects on the blood glucose level of the patient at the time point while reducing or distinguishing from clutter on the display.

16. The system of claim 15, further comprising:

a communication circuit, operably coupled to the one or more processors, configured to receive the two or more graphical representations; and wherein:

the one or more processors is/are configured to update the display for highlighting the two or more graphical representations when the time point is within the corresponding time windows.

17. The system of claim 15, wherein the one or more processors is/are configured to:

identify, based on a least a subset of the data streams, the time windows corresponding to the events, determine the two or more graphical representation of the events, generate a graph of blood glucose level over time for display, and update the display for highlighting the two or more graphical representations when the time point is within the corresponding time windows.

18. The system of claim 17, wherein:

the display is configured to display a first view before or without the user indication; and one or more processors is/are configured to update the display based on displaying a second view in response to the user indication, wherein the second view includes a format for the two or more graphical representations that different in format than other graphical representations.

19. The system of claim 18, wherein:

the first view represents the two or more graphical representations as summary icons among a set of selectable graphical representations, wherein, when unselected, the summary icons are smaller than the two or more graphical representations; and the second view includes a full-view of the two or more graphical representations.

20. The system of claim 15, wherein the display is configured to display detailed information in response to the user indication, wherein the detailed information includes a blood glucose reading, a number of steps, a calorie count, a menu item, an activity level, a representation thereof, or a combination thereof.

* * * * *